United States Patent [19]

Hergenrother et al.

[11] Patent Number: 5,877,336

[45] Date of Patent: Mar. 2, 1999

[54] IN THE SYNTHESIS OF TRIBUTYLTIN LITHIUM

[75] Inventors: William L. Hergenrother, Akron; Tristram W. Bethea, Bath, both of Ohio

[73] Assignee: Bridgestone Corporation, Tokyo, Japan

[21] Appl. No.: 775,852

[22] Filed: Dec. 31, 1996

[51] Int. Cl.$^6$ ....................................................... C07F 7/22
[52] U.S. Cl. .......................... 556/87; 526/173; 526/176; 526/190; 526/336; 526/335; 526/340; 524/571; 524/572; 524/575; 525/248; 525/370; 525/375; 525/332.3; 525/332.9; 525/331.9; 502/152
[58] Field of Search .................................. 556/87; 526/73, 526/76, 190, 335, 336, 340; 524/571, 572, 575; 525/248, 370, 375, 332.3, 332.9, 331.9; 502/152

[56] References Cited

U.S. PATENT DOCUMENTS 5,268,439  12/1993  Hergenrother et al. .
5,288,886  2/1994   Becker et al. ......................... 556/87 X
5,502,129  3/1996   Hergenrother et al. .

*Primary Examiner*—Paul F. Shaver
*Attorney, Agent, or Firm*—Daniel N. Hall

[57] ABSTRACT

Triorgano substituted-tin lithium initiators are made in a dimethyl ether solvent. The substitution of dimethyl ether as the solvent for the traditional tetrahydrofuran solvent results in an initiator for anionic polymerizations that can produce less 1,2-vinyl repeat units. The dimethyl ether is also easier to remove from the polymerization media because it has a boiling point at one atmosphere of minus 24.8° C. and thus is a gas at 25° C.

20 Claims, No Drawings

IN THE SYNTHESIS OF TRIBUTYLTIN LITHIUM

FIELD OF THE INVENTION

Triorgano substituted-tin lithium initiators for the anionic polymerization of rubbers are prepared in a dimethyl ether solvent at elevated pressures. The use of dimethyl ether as the solvent for the triorgano tin lithium is associated with the ability to form polymers having low 1,2-vinyl content from conjugated dienes.

BACKGROUND

U.S. Pat. No. 5,268,439 (W. Hergenrother, T. Bethea, and J. Doshak) disclosed that the use of elastomeric polymers prepared using triorgano substituted-tin lithium initiators in tires resulted in low hysteresis (e.g. low rolling resistance). The triorgano substituted tin of the initiators formed a functional end group on substantially each polymer chain and the tin containing functional group was associated with the lower hysteresis. Tetrahydrofuran (THF), tetramethylethylenediamine and diethylene methyl ether (diglyme) were listed as effective solvents (column 4, lines 26–28). Other polar solvents such as dimethyl ether gave unsatisfactory results (e.g. reaction did not go to completion or the initiator reacts with the solvent column 4, lines 28–33). In column 5, lines 2–27 it is disclosed that a polar coordinator (including tetrahydrofuran and dimethyl ether) may be added to promote randomization in copolymerization and to control vinyl content. The vinyl content of the resulting polymers of the patent examples were from 30 to 49 percent with the higher values being associated with the use of additional polar modifiers, in addition to the tetrahydrofuran associated with the initiator.

U.S. Pat. No. 5,502,129 (W. Hergenrother, W. Smith, A. Muratore, J. Sigle and M. Nemeth) disclosed a two step method of producing the triorgano substituted-tin lithium initiators which reduced the residual chloride content. The reduction in the chloride content was associated with reduced amounts of undesirable volatile organotin compound being released during subsequent processing of polymers produced with the triorgano substituted-tin lithium initiators. This patent generically groups solvents into 1) solvating or solubilizing solvents (which include tetrahydrofuran, glymes, and other ethers) and 2) alkanes. Tetrahydrofuran was the preferred solvating solvent and was used in all the examples. In the process a 3 to 6 fold molar excess of solvating solvent to triorgano tin was desired in the second step but a 0.5–2 fold excess was preferred in the first step to minimize the amount of soluble LiCl carried from the first step into the product.

SUMMARY OF THE INVENTION

Triorgano substituted-tin lithium initiators are prepared from bis(triorgano tin) and lithium metal in the presence of about three moles or more of dimethyl ether (DME) per mole of triorgano substituted-tin lithium formed. At the beginning of the reaction the dimethyl ether is typically at pressures of from 2 to 15 or 18 atmospheres at the reaction temperatures of from about 0° to about 65° C. As the triorgano substituted-tin lithium is formed about 3 moles of dimethyl ether are complexed with every mole of triorgano substituted-tin lithium according to the formula $R_3SnLi.(DME)_n$, where n is about 3 and where each R is independently a linear or cyclic alkyl group of 1 to 12 carbon atoms or an aryl or alkyl substituted aryl group of from 6 to 15 carbon atoms. The complexed moles of dimethyl ether contribute little to the pressure.

These initiators are useful for the anionic polymerization of conjugated diene monomers and optionally vinyl aromatic monomers into polymers. A particular utility of the initiators of the present invention is in forming polymers for tires such as tread rubber, carcass rubber, sidewall rubber, etc. The triorgano substituted-tin becomes an end group on the polymer and helps reduce the hysteresis at 20°–60° C. of the crosslinked compounded polymers. The dimethyl ether (not previously known to be useful as a solvent in forming tin lithium initiators) carried into the polymerization with these initiators does not cause the production of as much 1,2-vinyl structure during the anionic polymerization of conjugated dienes as does other solvents like tetrahydrofuran, tetramethylethylenediamine and diethylene glycol dimethyl ether. Increasing the amount of 1,2-vinyl structure in polymers from conjugated dienes increases their glass transition temperature which usually increases hysteresis losses at 20°–60° C. It is very desirable to be able to control the amount of 1,2-vinyl structure and thereby control hysteresis losses. Low hysteresis at 50°–60° C. is desirable for low rolling resistance which increases gasoline mileage.

DETAILED DESCRIPTION

The triorgano substituted-tin lithium initiators (also identified as a triorgano tin lithium dimethyl ether complex) can be prepared from the reaction of bis(triorganotin) with lithium metal. The mole ratio of lithium to bis(triorganotin) is desirably above 2:1 more desirably from about 2:1 to about 9:1, and preferably from about 2:1 to about 4:1. Extra moles of lithium may be separated from the initiator and reused in the process. It has generally been found that a polar solvent that complexes with and solubilizes the triorgano substituted-tin lithium needs to be present for the reaction to go forward. Tetrahydrofuran, tetramethylethylenediamine, and diethylene glycol dimethyl ether (diglyme) are polar solvents that were known to complex and solubilize triorgano substituted-tin lithium compounds. Applicants have found that dimethyl ether at temperatures from about 0° to about 65° C., more desirably from about 5° to about 40° C. and preferably from about 5° or 10° to about 25° or 30° C. and pressures above 1 atmosphere such as from about 2 to about 20 atmospheres, more desirably from about 3 to about 15 or 18 atmospheres, complexes and solubilizes the triorgano substituted-tin lithium. Polar solvents that did not complex and solubilize triorgano substituted-tin lithium compounds include diethylether, methyl tetrahydrofuran, and ethyl tetrahydrofuran. Thus the ability of polar solvents to complex with and solubilize tin lithium compounds appears to depend upon both having the right polarity and the correct physical size and shape to allow the polar solvent molecules to appropriately position themselves with respect to the tin lithium compound to solubilize and complex the triorgano substituted-tin lithium. If the complexing polar solvent is decreased significantly below the required amount the tin lithium compound is not formed.

The temperatures recited above allow the reaction to go substantially to completion in reasonable times and minimize side reactions that reduce the percentage of triorgano substituted-tin lithium produced. Desirably less than about 20 weight percent, more desirably less than 15 weight percent, preferably less than 10 weight percent and more preferably less than 5 weight percent of the total tin containing species in the reaction product are undesirable tetraalkyl tin side reaction products. Desirably less than 10 weight percent, more desirably less than 6 weight percent and preferably less than 4 weight percent of all tin containing species in the reaction product are other non-triorgano, substituted-tin lithium compounds. Desirably at least 90 weight percent and more preferably at least 93 weight percent of all tin containing species produced are triorgano substituted-tin lithium molecules.

Desirably at least about 3 moles of dimethyl ether are present per mole of triorgano substituted-tin lithium to be formed. This may be expressed as at least about 6 moles of dimethyl ether per mole of bis(triorganotin) because each mole of bis(triorganotin) can produce 2 moles of triorgano substituted-tin lithium. More desirably the mole ratio of dimethyl ether to triorgano substituted-tin lithium formed is from about 3 to about 50 and preferably from about 3 to about 10. Desirably the mole ratio of dimethyl ether to bis(triorgano substituted-tin) is from about 6 to about 100 and more desirably from about 6 to about 20.

Solvents other than dimethyl ether may be used in the reaction of bis(triorganotin) compounds with lithium metal. as long as at least 3 moles of dimethyl ether are present per mole of triorgano substituted tin lithium. The solvent for the reaction product may include non-polar solvent such as alkanes having from 4 to 24 carbon atoms. These alkanes do not solubilize lithium halides and can be used to wash out the reactor or other containers. Desirably the initiators are substantially free of polar solvents other than dimethyl ether. Substantially free of is used to mean that other polar solvents other than dimethyl ether and especially tetrahydrofuran, tetramethylethylenediamine, and diethylene glycol dimethyl ether are present in amounts less than 0.5 mole/mole of triorgano-tin lithium, more desirably less than 0.2 mole/mole of triorgano-tin lithium and preferably less than 0.1 mole/mole of triorgano-tin lithium in the composition.

The organo groups of the triorgano substituted-tin lithium can be branched, linear or cyclic alkyls having from 1 to 12 carbon atoms; aryls or alkyl substituted aryls having from 6 to 15 carbon atoms. Preferably they are alkyls having from 2 to 8 carbon atoms and most preferably they are butyl groups.

The bis(triorgano substituted-tin) having the formula $R_3SnSnR_3$ can be formed from the reaction of triorgano substituted-tin halide ($R_3SnX$) and lithium metal where R is as previously defined and X is a halide selected from Cl, Br, and I. Preferably the bis(triorgano substituted-tin) is formed by said reaction and soon thereafter is converted to triorgano substituted-tin lithiun having the formula $R_3SnLi$ or $R_3SnLi.(DME)_n$, where n is about 3 when shown as the complexed initiator. A byproduct of the first reaction is one mole of lithium halide for each mole of lithium and triorgano substituted-tin halide reactant. Desirably most of the lithium halide is removed from the rest of the reactants and products as an insoluble salt (e.g. as by filtration). The reaction desirably occurs between about 0° and about 65° C. As lithium halide may build up on the surface of the lithium metal retarding any reactions, it is desirable to use a high surface area form of lithium or agitate the lithium metal during the reaction to provide clean lithium metal surfaces. Polar solvents can dissolve a portion of the lithium halide formed that would otherwise deposit on the lithium metal. Providing clean lithium surfaces can expedite the reaction to form the bis (triorgano substituted-tin). However, as recited later in the specification, it is desirable to use limited amounts of polar solvents in this portion of the reaction where triorgano tin halide is converted to bis(triorganctin) so small amounts of lithium halide solubilized in polar solvents are carried forward. Polar solvents other than dimethyl ether present in the initiator and consequently the polymerization mixture increase the 1,2-vinyl content of the polymer from polymerizations of conjugated dienes. The exclusion of other polar solvents allows low vinyl polymers to be prepared if desired. The halide of the triorgano substituted-tin halide may be chloride, bromide or iodide but is preferably chloride.

The concentration of triorgano substituted-tin lithium in the reaction product from reacting bis(triorganotin) and lithium is desirably from about 0.01 to about 80 weight percent based upon the total weight of the triorgano substituted-tin lithium, the dimethyl ether, and any other solvents or reaction products. More desirably the amount of triorgano substituted-tin lithium is from about 10 to about 68 or 77 weight percent and preferably from about 20 to about 68 or 77 weight percent. These ranges can vary depending upon the amount of excess solvent and the ratio of the molecular weight of the triorgano substituted-tin lithium molecule to the molecular weight of dimethyl ether. The calculated weights of about 68 and 77 weight percent are based upon a tributyl and trioctyl substituted-tin lithium respectively. The upper limit of the weight percent triorgano substituted-tin lithium is created by the requirement that about 3 moles or more of dimethyl ether must be present for each mole of triorgano substituted-tin lithium. The molar ratio of lithium to triorgano substituted-tin is desirably about 1 but can vary depending on whether residual lithium or other tin containing compounds are present in the reaction product.

The inventive triorgano substituted-tin lithium initiator is fairly stable at room temperature and can be stored at 20°–25° C. without appreciable loss of activity as an anionic initiator for about 8 weeks or more. The triorgano substituted-tin lithium initiator desirably has a low halide content such that the halide content is desirably below 3,000 or 3,500 ppm, more desirably below 2,000 or 2,500 ppm and preferably from about 100 or 200 to about 1,500 ppm based upon the weight of the triorgano substituted-tin lithium. Low halide content is desirable as the halides are typically carried forward with the polymer formed from an anionic polymerization. Halides with their lithium counterion present in the polymer promote a reaction where the triorgano substituted-tin terminal groups detach from the polymer and become triorgano tin halide molecules while the polymer is compounded and crosslinked. The detached triorgano substituted-tin halide groups are volatile, have an undesirable odor, and are an environmental concern. Chloride is the preferred halide in the starting materials and is therefore the preferred halide contaminant.

Equipment for the reaction of bis(triorgano substituted-tin) with lithium metal and/or for the reaction of triorgano substituted-tin halide is desirably inert to lithium metal. Examples of suitable materials include polyethylene, polypropylene, stainless steel, carbon steel, glass, etc. The materials need to be of sufficient strength to withstand the pressures of from about 2 to about 15 or 18 atmospheres developed with the dimethyl ether. Desirably the gases used to purge the reactors are gases inert to lithium such as argon or helium. These gases are desirably dried to remove water.

Triorgano substituted-tin lithium initiators are useful for the anionic polymerization of conjugated dienes and optionally vinyl aromatic monomers. The conjugated diene monomers desirably have from about 4 to about 12 carbon atoms and more desirably from about 4 to about 8 carbon atoms such as butadiene and isoprene. The vinyl aromatic monomers desirably have from 8 to 18 carbon atoms such as styrene. Other monomers capable of anionic polymerization may be polymerized or copolymerized using these triorgano substituted-tin lithium initiators. These include cyclic ethers and lactones. Other monomers may be copolymerized with the conjugated dienes and optional vinyl aromatic monomers. Desirably the repeat units from said conjugated dienes and any optional vinyl aromatic monomers are at least 70 mole %, desirably at least 80 mole %, more desirably at least 90 mole % and preferably at least 95 mole % of all repeat units in the polymer(s) formed. Polymers and copolymers of particular interest are polybutadienes and copolymers of styrene and butadiene.

The polymerization of conjugated dienes such as 1,3-butadiene having the structure $CH_2=CH-CH=CH_2$ results in a repeat unit with only one carbon to carbon double bond of the formula

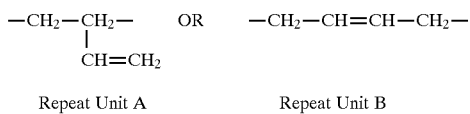

Repeat Unit A          Repeat Unit B

Repeat unit A is called a 1,2-vinyl addition repeat unit derived from butadiene. It is so named because the polymer backbone only extends through the 1st and 2nd carbon atoms of the butadiene and a pendant vinyl unit remains. Repeat unit B is called a 1,4-repeat unit because the polymer backbone extends continuously from the first to the 4th carbon of the butadiene precursor. The 1,4-repeat unit can be in a cis or trans configuration and that will also affect the glass transition temperature (Tg). It is understood that due to the symmetry of the butadiene monomer some of the 1,2-vinyl units are in reality 4,3-vinyl units but since the 1,2-vinyl unit cannot be distinguished from a 4,3-vinyl unit in the final polymer a single 1,2-vinyl designation is used. A generic name for repeat units having a pendant vinyl unit from conjugated dienes is vinyl addition structures.

Methods of anionically polymerizing elastomers using triorgano substituted-tin lithium initiators are disclosed in U.S. Pat. No. 5,268,439 which is herein incorporated by reference for its teachings thereon. The triorgano tin lithium dimethyl ether complexes of this invention are an improvement over the initiators of U.S. Pat. No. 5,268,439 because the dimethyl ether has a significantly reduced tendency to promote 1,2-vinyl addition from the conjugated diene monomers at usual polymerization temperatures (25° to about 150° C.) as compared to tetrahydrofuran complexed triorgano substituted-tin lithium initiators. The reduction of the 1,2-vinyl addition of the conjugated diene monomers produces a polymer with a lower glass transition temperature (Tg) which usually results in desirably lower hysteretic properties at. temperatures from about 20° to about 60° C. when compounded and crosslinked into vulcanized articles such tires.

Alternatively, polymers or copolymers anionically polymerized with triorgano tin lithium dimethyl ether complexes may tolerate additional styrene into the copolymer (which raises the Tg). Increased amounts of styrene provide improved properties in vulcanized articles such as wear resistance. Thus the use of dimethyl ether instead of tetrahydrofuran as an organo tin complexing agent results in initiators that can yield a lower 1,2-vinyl content thereby allowing the preparation of polymers of equivalent Tg with higher weight percents of styrene. Alternatively an optimized amount of Tg Lowering and styrene increase can occur.

In some embodiments the amount of additional polar modifiers used in anionic polymerizations is small or nil when the triorgano tin lithium dimethyl ether complexes are used as an initiator. In other embodiments polar modifiers are added prior to or during the polymerization. The amount of 1,2-vinyl enchainment thus is desirably limited to from about 8 to about 65 mole percent of the total repeat units derived from the polymerization of conjugated dienes, more preferably it is from about 8 or 10 to about 40 mole percent and most preferably when nil or small amounts of polar modifiers are present it is from about 8 or 10 to about 30 mole percent.

EXAMPLES

The following examples illustrate how to prepare triorgano tin lithium initiator and the use of that initiator to anionically produce a styrenebutadiene copolymer.

Comparative Example A

Preparing initiator with tetrahyrofuran starting at 24° C. Lithium wire (15.0 g, 2.14 mole), tributyl tin chloride (57 g, 0.175 mole) and tetrahydrofuran (60 g, 0.832 mole) were reacted in a 316 stainless steel bomb reactor under argon with stirring overnight. An analysis of the yellow-green liquid reaction product indicated the total base was 1.49M, the free base was 0.13M, and the active base was 1.36M. The active base is a measure of the organo lithium initiator and the free base is a measure of the residual dissolved lithium. The presence of a yellow-green color is an indication that the tributyl tin chloride was converted to tributyl tin lithium. The percent of active tributyltin lithium (TBTL) initiator was 91.4 based upon the amount of tributyl tin chloride.

Comparative Example B

Preparing initiator in dimethyl ether at −25° C. Lithium (0.25 g, 0.036 mole), tributyl tin chloride (4.21 g, 0.013 mole), and dimethyl ether (3.3 g, 0.072 mole) were reacted at the reflux temperature of the dimethyl ether (−25° C.) for two hours. The addition sequence was to add the lithium to a 4 necked reaction vessel purged with argon and maintained under argon at all times. The vessel was fitted with a condenser, a magnetic stir bar, 2 stopcocks and a septum. Dimethyl ether was transferred to the reactor by condensing dimethyl ether gas using a condenser chilled with dry ice. Then the tributyltin chloride was injected into the reactor through the septum. The dry ice was maintained in the condenser and the dimethyl ether refluxed in the stirred reactor for 2 hours. Since a yellow to green color characteristic of tributyl tin lithium did not appear the reaction to form tributyl tin lithium did not occur. This experiment illustrates that dimethyl ether at low temperature and low pressure (−25° C. and 1 atmosphere) does not facilitate the conversion of tributyl tin chloride to tributyl tin lithium (TBTL)

Inventive Example 1

Preparing initiator in dimethyl ether starting at about 24° C. Lithium (recovered as unreacted metal from Example A about 12.6 g, 1.8 moles), tributyl tin chloride (60 g, 0.184 mole) and dimethyl ether (44.4 g, 0.964 mole) were reacted in a 316 stainless steel bomb reactor at about 4 atmospheres pressure on a shaker overnight. An analysis of the yellow-green liquid reaction product indicated total base was 1.50M, free base was 0.15M, active base was 1.35M. The percent of active tributyltin lithium (TBTL) initiator was 90.3 based upon the amount of tributyl tin chloride. This experiment illustrates that dimethyl ether at 24° C. and above 2 atmospheres pressure facilitates the conversion of tributyltin chloride to tributyl tin lithium.

Comparative Examples C and Inventive Example 2

Two tributyltin lithium initiators (one made with tetrahydrofuran, Comparative Example A; and the other with dimethyl ether, Example 2) were used in anionic polymerizations of butadiene. Two 32 oz. beverage bottles were cleaned, dried, capped with a rubber septum and nitrogen purged. The following reagents were added, polymerization occurred, and the polymers resulting therefrom were analyzed.

| Example | Comp. Ex. C | Ex. 2 |
|---|---|---|
| 24.4% butadiene in hexane by wt. | 370.3 g | 360.2 g |
| Tributyltin lithium from Ex. | A | 1 |
| Solvent used to make TBTL | THF | DME |
| Amount added | 0.27 ml | 0.27 ml |
| Polymerization temp & time | 50° C. & 3 days | 50° C. & 3 days |
| Polymer isolated | 90 g | 88.2 g |
| Tg (onset) | −85.1° C. | −92.9° C. |
| Mn | 223,000 g/mol | 206,000 g/mol |
| Mw/Mn | 1.25 | 1.11 |
| 1,2-vinyl content | 20.7 mole % | 10.8 mole % |

Inventive Examples 3–4 and Comparative Examples D, E and F

Styrene-butadiene rubbers (SBRs) were prepared by anionic polymerizations. The procedure and significant properties are listed below and in the following table. To a 2 gal. (7.6 L) reactor was added 1.68 lbs (0.763 kg) of 33 wt. % styrene in hexane, 4.56 lbs (2.070 kg) of 31.3 wt. % butadiene in hexane and 4.77 lbs (2.166 kg) of hexane. The polymerization was done both with and without added polar modifiers using TBTL initiators that had either been prepared with tetrahydrofuran (THF) or dimethyl ether (DME). The general procedure was such that the monomers, hexane and modifiers were all heated in the clean dry nitrogen purged reactors to 24.4° C. before adding the initiator and heating to 54° C. At this temperature the jacket water was turned off and the reaction was allowed to exotherm to the peak temperature indicated. After 5 minutes at this temperature a 1/1 equivalent mixture of tributyltin chloride and tin tetrachloride was added. The polymer solution was cooled dropped into alcohol containing dibutyl p-cresol and drum dried.

desirable lower rolling resistance or improved traction. In order to minimize the effect of the different polymer Tgs that were involved, blends were made to give comparable Tg to the SBRs being compared. The samples and tan δ obtained are as follows.

| Example | G | 5 | H | 6 |
|---|---|---|---|---|
| Initiator solvent | THF | DME | THF | DME |
| Polymers used | 7 & 10 | 8 | 8 | 6 & 8 |
| Tg | −44° C. | −44° C. | −55° C. | −55° C. |
| Tan δ @ 50° C. | 0.095 | 0.101 | 0.102 | 0.099 |
| Tan δ @ 0° C. | 0.205 | 0.214 | 0.174 | 0.167 |

The data show that the tan δ reduction mechanism using triorganotin lithium initiators is the same for copolymers prepared with both THF and DME. The Tg values and the tan δ values are not appreciably different for SBRs prepared from TBTL complexed with DME than for TBTL complexed with THF because of the polar modifiers used in the polymerizations of example 3 and 4. A low tan δ at 50° C. is desirable as it indicates the rubber will give a low rolling resistance relative to rubber with a higher tan δ at the operational temperature of most tires (about 50° C.). A high tan δ at 0° C. indicates a rubber will probably impart good traction and stopping characteristics in a tire tread.

While in accordance with the patent statutes the best mode and preferred embodiment has been set forth, the scope of the invention is not limited thereto, but rather by the scope of the attached claims.

What is claimed is:

1. A process for preparing triorgano substituted-tin lithium, comprising;
    the step of reacting lithium metal with bis(triorganotin) in the presence of dimethyl ether at a temperature from about 0° C. to about 65° C. thus forming triorgano substituted-tin lithium dimethyl ether complex,
    wherein the mole ratio of dimethyl ether to bis (triorganotin) is at least 6:1, and
    wherein the pressure of said dimethyl ether in said step before formation of said triorgano substituted-tin lithium about 2 to about 20 atmospheres.

| Example | 3 | D | 4 | E | F |
|---|---|---|---|---|---|
| Initiator solvent | DME | THF | DME | THF | THF |
| Initiator conc. | 1.6M | 1.14M | 1.6M | 1.14M | 1.14M |
| Amount used | 4.53 ml | 6.32 ml | 4.53 ml | 6.32 ml | 6.32 ml |
| Polar modifier* | 4.07 mM | 0 | 8.14 mM | 4.07 mM | 7.73 mM |
| Temp. max °C. | 112 | 96 | 106 | 114 | 93 |
| Time to temp max | 8 min. | 9. min. | 9 min. | 7. min. | 12 min. |
| Tg of polymer | −61° C. | −66° C. | −44° C. | −55° C. | −31° C. |
| 1,2-vinyl content of Bd portion | 25% | 20% | 36% | 29% | 46% |
| Styrene content | 31% | 28% | 30% | 30% | 30% |

*The polar modifier was an oligomeric oxolanyl alkane polar coordinator as described in U.S. Pat. No. 4,429,091.

These copolymers were compounded in a carbon black- and oil-containing rubber formulation in order to evaluate the variation of tan δ caused by the use of different TBTL initiators. Tan δ is a way to numerically quantify hysteresis loss at specific testing frequency and temperature. Lower tan δ values indicate lower hysteresis losses but a direct conversion from tan δ to a hysteresis measurement such as % rebound are not generally made. Tan δ values are preferred for vehicle tire analysis because slight shifts in tan δ at specific frequencies and temperatures can be correlated with 2. A process according to claim 1, further including the step of reacting a triorgano substituted-tin halide with lithium to produce said bis(triorgano-tin) and lithium halide, and wherein said triorgano substituted-tin lithium is substantially free of tetrahydrofuran, tetramethylethylenediamine and diethylene glycol dimethyl ether.

3. A process according to claim 2, wherein the majority by weight of said lithium halide is separated from said bis (triorganotin) before it is converted to triorgano substituted-tin lithium and wherein the mole ratio of dimethyl ether to bis(triorganotin) is from about 6 about 20.

4. A process according to claim 1, wherein said bis (triorganotin) is a bis(trialkyltin) and each alkyl has from 1 to 12 carbon atoms.

5. A process according to claim 4, wherein said bis (tricrganotin) is bis(tributyltin).

6. A process according to claim 3, wherein said triogano substituted-tin halide is a trialkyl substituted-tin halide and wherein each alkyl has from 1 to 12 carbon atoms.

7. A process according to claim 6, wherein said halide is chloride.

8. A process according to claim 7, wherein the trialkyl substituted-tin chloride is tributyl substituted-tin chloride, wherein said pressure is from about 3 to about 18 atmospheres.

9. A process for preparing a triorgano tin lithium dimethyl ether complex, $R_3SnLi.(DME)_n$, where n is about 3, which comprises the steps of
(a) reacting a triorganotin halide, $R_3SnX$, with lithium metal to produce a bis(triorgano tin),
(b) separating the majority of the LiX from the $R_3Sn$—$SnR_3$, then
(c) reacting said $R_3Sn$—$SnR_3$ with lithium metal in the presence of dimethyl ether, DME, at a temperature from about 0° C. to about 65° C. and a DME pressure from about 2 to about 20 atmospheres to form $R_3SnLi.(DME)_n$, where n is about 3,
wherein each R is independently a linear or cyclic alkyl group of from 1 to 12 carbon atoms or an aryl or alkyl substituted aryl of from 6 to 15 carbon atoms, and X i a halide selected from Cl, Br, and I.

10. A process according to claim 9, wherein said dimethyl ether in step (c) is present in amounts from 6 to 20 moles per mole of $R_3Sn$—$Sn$—$R_3$, said pressure is from about 3 to about 18 atmospheres, said halide is chloride, R is independently an alkyl of from 2 to 8 carbon atoms, and said triorgano tin lithium dimethyl ether complex is substantially free of tetrahydrofuran, tetramethylethylenediamine, and diethylene glycol dimethyl ether.

11. A triorgano substituted-tin lithium initiator composition, comprising;
(i) triorgano substituted-tin lithium complexed with about 3 moles of dimethyl ether per mole of triorgano substituted-tin lithium, and
optionally (ii) having nonpolar alkane solvents and/or additional dimethyl ether.

12. An initiator composition according to claim 11, wherein said triorgano substituted-tin lithium is trialkyl substituted-tin lithium, wherein each alkyl group independently has from 1 to 12 carbon atoms, and wherein said initiator solution is substantially free of tetrahydrofuran, tetramethylethylenediamine, and diethylene glycol dimethyl ether.

13. An initiator composition according to claim 12, wherein said dimethyl ether and trialkyl substituted-tin lithium form a complex soluble in a hydrocarbon solvent with a mole ratio of dimethyl ether to trialkyl substituted-tin lithium of from about 3 to about 10.

14. An initiator composition according to claim 13, wherein each said alkyl group has from 2 to 8 carbon atoms.

15. An initiator composition according to claim 14, wherein each alkyl group is a butyl group.

16. A process for anionically polymerizing an elastomeric polymer from at least one conjugated diene monomer having from 4 to 8 carbon atoms and optionally one or more monovinyl aromatic monomers including the steps of combining a solvent, said conjugated diene, and a triorgano substituted-tin lithium initiator, initiating the anionic polymerization of at least said one conjugated diene with said triorgano tin substituted-tin lithium initiator, and subsequently terminating the anionic polymerization, said triorgano substituted-tin lithium initiator being complexed with dimethyl ether wherein about 3 or more moles of dimethyl ether are present per mole of triorgano substituted-tin lithium.

17. A process according to claim 16, wherein the at least one conjugated diene forms repeat units having from about 8 to about 65 mole percent vinyl addition structures and said initiator being substantially free of tetrahydrofuran, tetramethylethylenediamine, and diethylene glycol dimethyl ether.

18. A process according to claim 17, wherein said at least one conjugated diene forms repeat units having from about 8 to about 40 mole percent vinyl addition structures.

19. A process according to claim 18, wherein said at least one conjugated diene comprises butadiene and/or isoprene and forms repeat units having from about 8 to about 30 mole percent vinyl addition structures.

20. An elastomeric polymer made by the process of claim 16.

* * * * *